US012570041B2

(12) United States Patent
Eideloth

(10) Patent No.: US 12,570,041 B2
(45) Date of Patent: Mar. 10, 2026

(54) BUILD MATERIAL HANDLING UNIT FOR A POWDER MODULE FOR AN APPARATUS FOR ADDITIVELY MANUFACTURING THREE-DIMENSIONAL OBJECTS

(71) Applicant: Concept Laser GmbH, Lichtenfels (DE)

(72) Inventor: Dominik Eideloth, Edensfeld (DE)

(73) Assignee: Concept Laser GmbH, Lichtenfels (DE)

( * ) Notice: Subject to any disclaimer, the term of this patent is extended or adjusted under 35 U.S.C. 154(b) by 0 days.

(21) Appl. No.: 18/400,044

(22) Filed: Dec. 29, 2023

(65) Prior Publication Data

US 2024/0131783 A1 Apr. 25, 2024

Related U.S. Application Data

(62) Division of application No. 17/737,336, filed on May 5, 2022, now Pat. No. 11,878,463, which is a division
(Continued)

(30) Foreign Application Priority Data

Dec. 20, 2018 (EP) ..................................... 18214640

(51) Int. Cl.
*B29C 64/00* (2017.01)
*B01D 67/00* (2006.01)
(Continued)

(52) U.S. Cl.
CPC ...... *B29C 64/194* (2017.08); *B01D 67/00045* (2022.08); *B01D 67/00415* (2022.08);
(Continued)

(58) Field of Classification Search
CPC .............................. B29C 64/194; B33Y 10/00
See application file for complete search history.

(56) References Cited

U.S. PATENT DOCUMENTS

| | | | |
|---|---|---|---|
| 6,429,402 | B1 | 8/2002 | Dixon et al. |
| 2002/0090410 | A1 | 7/2002 | Tochimoto et al. |

(Continued)

FOREIGN PATENT DOCUMENTS

| | | |
|---|---|---|
| EP | 2957365 A1 | 12/2015 |
| WO | WO2017/100695 A1 | 6/2017 |
| WO | WO2018/022002 A1 | 2/2018 |

OTHER PUBLICATIONS https://www.youtube.com/watch?v=16bUw6kBm1k (Year: 2020).*
(Continued)

*Primary Examiner* — Nicholas Krasnow
(74) *Attorney, Agent, or Firm* — Wood Herron & Evans LLP

(57) ABSTRACT

Build material handling unit for a powder module for an apparatus for additively manufacturing three-dimensional objects, which apparatus is adapted to successively layer-wise selectively irradiate and consolidate layers of a build material which can be consolidated by means of an energy source, wherein the build material handling unit is coupled or can be coupled with a powder module, wherein the build material handling unit is adapted to level and/or compact a volume of build material arranged inside a powder chamber of the powder module by controlling the gas pressure inside the powder chamber.

15 Claims, 1 Drawing Sheet

Figure 1:
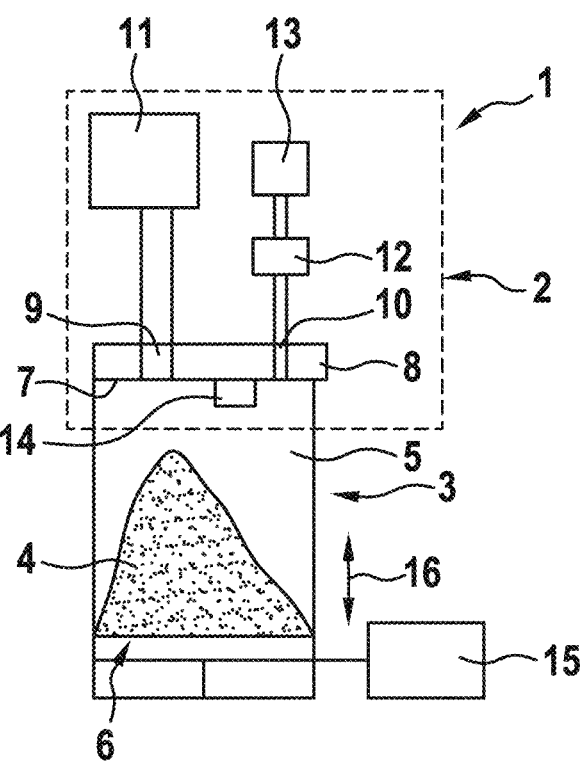

Related U.S. Application Data of application No. 16/293,635, filed on Mar. 5, 2019, now Pat. No. 11,331,858.

(51) Int. Cl.

| | |
|---|---|
| *B01L 5/00* | (2006.01) |
| *B22F 10/00* | (2021.01) |
| *B22F 10/32* | (2021.01) |
| *B22F 10/85* | (2021.01) |
| *B22F 12/00* | (2021.01) |
| *B22F 12/60* | (2021.01) |
| *B22F 12/82* | (2021.01) |
| *B29C 64/10* | (2017.01) |
| *B29C 64/176* | (2017.01) |
| *B29C 64/182* | (2017.01) |
| *B29C 64/194* | (2017.01) |
| *B29C 64/20* | (2017.01) |
| *B29C 64/205* | (2017.01) |
| *B29C 64/227* | (2017.01) |
| *B29C 64/245* | (2017.01) |
| *B29C 64/25* | (2017.01) |
| *B29C 64/255* | (2017.01) |
| *B29C 64/30* | (2017.01) |
| *B29C 64/307* | (2017.01) |
| *B29C 64/386* | (2017.01) |
| *B29C 64/393* | (2017.01) |
| *B29C 64/40* | (2017.01) |
| *B29C 65/82* | (2006.01) |
| *B33Y 10/00* | (2015.01) |
| *B33Y 30/00* | (2015.01) |
| *B33Y 40/00* | (2020.01) |
| *B33Y 40/10* | (2020.01) |
| *B33Y 40/20* | (2020.01) |
| *B33Y 50/00* | (2015.01) |
| *B33Y 50/02* | (2015.01) |
| *B33Y 70/00* | (2020.01) |
| *B33Y 80/00* | (2015.01) |
| *B33Y 99/00* | (2015.01) |
| *B22F 10/10* | (2021.01) |
| *B28B 1/00* | (2006.01) |
| *G01N 1/28* | (2006.01) |
| *G01N 21/956* | (2006.01) |
| *G01N 23/2251* | (2018.01) |
| *G01N 33/50* | (2006.01) |
| *G02B 21/34* | (2006.01) |
| *G03F 7/00* | (2006.01) |
| *H01J 37/20* | (2006.01) |
| *H01J 37/32* | (2006.01) |

(52) U.S. Cl.
CPC ................ *B01L 5/00* (2013.01); *B22F 10/00* (2021.01); *B22F 10/32* (2021.01); *B22F 10/85* (2021.01); *B22F 12/00* (2021.01); *B22F 12/60* (2021.01); *B22F 12/82* (2021.01); *B29C 64/00* (2017.08); *B29C 64/10* (2017.08); *B29C 64/176* (2017.08); *B29C 64/182* (2017.08); *B29C 64/20* (2017.08); *B29C 64/205* (2017.08); *B29C 64/227* (2017.08); *B29C 64/245* (2017.08); *B29C 64/25* (2017.08); *B29C 64/255* (2017.08); *B29C 64/30* (2017.08); *B29C 64/307* (2017.08); *B29C 64/386* (2017.08); *B29C 64/393* (2017.08); *B29C 64/40* (2017.08); *B29C 65/8253* (2013.01); *B33Y 10/00* (2014.12); *B33Y 30/00* (2014.12); *B33Y 40/00* (2014.12); *B33Y 40/10* (2020.01); *B33Y 40/20* (2020.01); *B33Y 50/00* (2014.12); *B33Y 50/02* (2014.12); *B33Y 70/00* (2014.12); *B33Y 80/00* (2014.12); *B33Y 99/00* (2014.12); *B22F 10/10* (2021.01); *B28B 1/001* (2013.01); *B29C 65/8292* (2013.01); *G01N 1/28* (2013.01); *G01N 2021/95676* (2013.01); *G01N 23/2251* (2013.01); *G01N 33/50* (2013.01); *G01N 2223/418* (2013.01); *G02B 21/34* (2013.01); *G03F 7/70416* (2013.01); *G03G 2215/2054* (2013.01); *G05B 2219/49023* (2013.01); *G05B 2219/49246* (2013.01); *G06T 2207/10061* (2013.01); *G06V 2201/122* (2022.01); *H01J 37/20* (2013.01); *H01J 37/3244* (2013.01); *H01J 2237/006* (2013.01); *H01J 2237/2003* (2013.01); *H01J 2237/2608* (2013.01); *Y10S 148/143* (2013.01); *Y10T 156/1722* (2015.01); *Y10T 156/1798* (2015.01)

(56) References Cited

U.S. PATENT DOCUMENTS

| | | | |
|---|---|---|---|
| 2007/0126157 A1 | 6/2007 | Bredt | |
| 2009/0255912 A1 | 10/2009 | Dietrich | |
| 2012/0251378 A1 | 10/2012 | Abe et al. | |
| 2015/0367448 A1* | 12/2015 | Buller | H05B 6/68 |
| | | | 219/74 |
| 2018/0065303 A1 | 3/2018 | Schade | |
| 2018/0200792 A1 | 7/2018 | Redding et al. | |
| 2018/0272604 A1 | 9/2018 | Welch | |
| 2019/0118263 A1 | 4/2019 | Buller et al. | |
| 2019/0126347 A1 | 5/2019 | Roman et al. | |
| 2019/0151945 A1 | 5/2019 | Okazaki | |
| 2019/0322051 A1 | 10/2019 | Wakelam et al. | |
| 2020/0061655 A1 | 2/2020 | Wakelam et al. | |
| 2020/0147866 A1 | 5/2020 | Van Egmond | |

OTHER PUBLICATIONS

Marlin Steel, Sintering vs Melting: What's the Difference? American Manufacturing, Feb. 6, 2020, 8 Pages. https://www.marlinwire.com/blog/metal-forming-faqs-whats-the-difference-of-sintering-vs-melting#:~:text=Sintering%20combines%20by%20heat,if%20enugh%pressure%20is%20applied.

Smith, Laser Sintering vs Laser Melting, Additiva, 2021, 3 Pages. https://www.additivalab.com/laser-sintering-vs-laser-melting/.

\* cited by examiner

BUILD MATERIAL HANDLING UNIT FOR A POWDER MODULE FOR AN APPARATUS FOR ADDITIVELY MANUFACTURING THREE-DIMENSIONAL OBJECTS

CROSS-REFERENCE TO RELATED APPLICATIONS

This application is a divisional application of U.S. application Ser. No. 17/737,336, filed on May 5, 2022, which is a divisional application of U.S. application Ser. No. 16/293,635, filed on Mar. 5, 2019, which claims priority to European Patent Application Serial No. 18 214 640.7 filed Dec. 20, 2018, the contents of each of which are herein incorporated in their entirety by reference.

DESCRIPTION

The invention relates to a build material handling unit for a powder module for an apparatus for additively manufacturing three-dimensional objects, which apparatus is adapted to successively layerwise selectively irradiate and consolidate layers of a build material which can be consolidated by means of an energy source.

Apparatuses for additively manufacturing three-dimensional objects are generally known from prior art. Usually, build material is provided in a build plane, e.g. conveyed from a dose plane to a build plane inside a process chamber of the apparatus. For providing the build material it is necessary to store the build material in a powder chamber of a powder module from which powder chamber the build material can be provided to be applied in the build plane. For example, the apparatus may comprise a dose module with a dose chamber in which fresh build material can be stored and provided from the dose chamber to a dose plane. The build material provided in the dose plane may be conveyed, e.g. via an application element of an application unit, such as a rake or a re-coater blade, to the build plane in which it is (evenly) distributed and afterwards (selectively) consolidated, e.g. via irradiation with an energy beam.

Further, it is known from prior art that the powder module has to be refilled, e.g. after an additive manufacturing process is finished or, if a fill level inside the powder chamber of the powder module reaches a defined level, in particular, if the powder module is empty. By (re-) filling build material into the powder module, it is advantageous, if the build material is compacted and leveled, in that an even surface of build material may be provided, e.g. in a dose plane, from where the build material can be picked up via the application element to be distributed in the build plane. As, for example due to dropping the build material into the powder chamber of the powder module, the build material is not automatically distributed evenly and compacted in the powder module, different types of build material handling units are known, such as scrapers, vibrating units and the like that are used to (mechanically) compact and/or a level the build material that is filled into the powder module. These known units are complex and usually involve a direct mechanical interaction with the build material for leveling and/or compaction of the build material inside the powder chamber of the powder module.

It is an object of the present invention to provide an improved build material handling unit for a powder module, wherein in particular a less complex set up allows for a proper leveling and compaction of the build material arranged inside a powder chamber of a powder module.

The object is inventively achieved by a build material handling unit according to claim 1. Advantageous embodiments of the invention are subject to the dependent claims.

The build material handling unit described herein is a build material handling unit for an apparatus for additively manufacturing three-dimensional objects, e.g. technical components, by means of successive selective layerwise consolidation of layers of a powdered build material ("build material") which can be consolidated by means of an energy source, e.g. an energy beam, in particular a laser beam or an electron beam. A respective build material can be a metal, ceramic or polymer powder. A respective energy beam can be a laser beam or an electron beam. A respective apparatus can be an apparatus in which an application of build material and a consolidation of build material is performed separately, such as a selective laser sintering apparatus, a selective laser melting apparatus or a selective electron beam melting apparatus, for instance. Alternatively, the successive layerwise selective consolidation of build material may be performed via at least one binding material. The binding material may be applied with a corresponding application unit and, for example, irradiated with a suitable energy source, e.g. a UV light source.

The apparatus may comprise a number of functional units which are used during its operation. Exemplary functional units are a process chamber, an irradiation device which is adapted to selectively irradiate a build material layer disposed in the process chamber with at least one energy beam, and a stream generating device which is adapted to generate a gaseous fluid stream at least partly streaming through the process chamber with given streaming properties, e.g. a given streaming profile, streaming velocity, etc. The gaseous fluid stream is capable of being charged with non-consolidated particulate build material, particularly smoke or smoke residues generated during operation of the apparatus, while streaming through the process chamber. The gaseous fluid stream is typically inert, i.e. typically a stream of an inert gas, e.g. argon, nitrogen, carbon dioxide, etc.

As described before, the invention relates to a build material handling unit for a powder module for an additive manufacturing apparatus. Thus, the build material handling unit can be used to level and/or compact the volume of build material that is arranged inside the powder chamber of the powder module. The invention is based on the idea that the build material handling unit is coupled or can be coupled with a powder module, wherein the build material handling unit is adapted to level and/or compact a volume of build material arranged inside a powder chamber of the powder module by controlling the gas pressure inside the powder chamber.

In other words, it is possible to couple the build material handling unit with the powder module, e.g. by releasable connecting the powder module with the build material handling unit or vice versa. For example, the opening in the powder module, e.g. through which build material can be provided in a dose plane, can be attached to the build material handling unit. By controlling the pressure inside the powder chamber of the powder module, it is possible to compact and level the build material inside the powder chamber at the same time. Hence, it is not necessary to use a complex mechanical setup for mechanically leveling and compacting the volume of build material in the powder chamber, but it is advantageously sufficient to control the gas pressure inside the powder chamber and thereby compact and level the build material.

Thus, it is possible that the gas that streams into or out of the volume of build material, e.g. into or out of the powder chamber, as the gas pressure inside the powder chamber is controlled, fluidizes the build material and therefore, realizes a compaction and a leveling of the build material. Hence, advantageously, the mechanical contact between the build material handling unit and the build material arranged in the powder chamber is not necessary. Instead, the build material handling unit can be coupled with the powder module, e.g. via a pipe structure, in that the gas pressure inside the powder module can be controlled. It is also possible that the build material handling unit remains coupled with the powder module, e.g. by integrating a build material handling unit in the powder module, in particular a dose module or an overflow module.

In particular, the build material handling unit may be adapted to generate an overpressure or a negative pressure, preferably a vacuum, inside the powder chamber of the powder module. Hence, it is possible to control the pressure inside the powder chamber, as described before, wherein in particular an overpressure or a negative pressure can be generated. For example, as the powder chamber is usually flooded with inert gas, the inert gas may be at least partially removed from the powder chamber to generate a negative pressure or more inert gas may be guided into the powder chamber to generate an overpressure in the powder chamber. It is particularly preferred that the build material handling unit is adapted to generate a negative pressure, e.g. by removing inert gas from the powder chamber. The inert gas that escapes from the volume of build material arranged in the powder chamber fluidizes the build material and thereby compacts and levels the (powdery) build material.

Preferably, the build material handling unit may be adapted to generate a leveling state with a first negative pressure, preferably between 0.7-1 bar, in particular between 0.8-0.9 bar. The negative pressure above relates to the absolute pressure generated in the powder chamber via the build material handling unit. Of course, it is also possible to specify the negative pressure as relative pressure, e.g. compared to an ambient atmosphere.

Thus, for leveling the build material it is sufficient to generate a relatively low negative pressure, wherein the leveling process already starts with applying the negative pressure. Usually, the leveling process is finished by applying a relative negative pressure of about 0.1 bar, wherein of course, the leveling effect depends on the size of the build chamber, the type of build material, the amount of build material and the degree of unevenness with respect to the surface of build material. Hence, the leveling of build material may be understood as continuous process starting with the control or the variance of the gas pressure inside the powder chamber, wherein usually the leveling and an even upper surface of build material can be reached with generating a relatively low differential pressure compared to the initial pressure inside the powder chamber. Thus, it is possible to generate a negative pressure inside the powder chamber to fluidize the build material allowing for a movement of the build material and thereby, forming an even surface at the top of the volume of build material.

According to another embodiment of the inventive build material handling unit, the build material handling unit may be adapted to generate a compacting state with a second negative pressure, preferably between 0.01-1 bar, in particular between 0.1-0.9 bar. Hence, it is possible to perform a continuous compacting process by generating a second negative pressure. Preferably, the second negative pressure is below the first negative pressure, wherein both pressure intervals overlap. Thus, the compaction process starts by applying the negative pressure in the powder chamber of the powder module, wherein the compaction degree of the volume of build material in the powder chamber can be increased, e.g. continuously, dependent on the relative pressure applied in the powder chamber.

Therefore, it is possible to simultaneously level and compact the build material arranged in the powder chamber by applying the negative pressure in the gas atmosphere inside the powder chamber. Hence, inert gas may be removed from the powder chamber allowing for a leveling state and a compacting state to be reached and thereby, leveling and compacting the build material. Of course, afterwards the gas pressure inside the powder chamber can be restored to its initial value, e.g. atmosphere pressure or a slight overpressure compared to the ambient air.

The inventive build material handling unit may further be improved by providing a connection element, preferably a connection plate, that is adapted to connect the build material handling unit with the powder module, in particular to seal an opening of the powder chamber of the powder module. According to this embodiment, it is possible that the powder module and the build material handling unit may be coupled to each other via the connection element. The connection element is connected to the powder module and thereby, seals an opening of the powder chamber of the powder module. Usually, the powder module is open at the top for providing build material in the additive manufacturing process. For example, the powder module has a carrying element for carrying the build material which is arranged inside the powder chamber and can be moved, in particular raised and lowered for receiving more build material or for providing build material in the additive manufacturing process. This opening is sealed by the connection element, which is preferably a plate-like base body. Hence, by connecting the build material handling unit via the connection element with the powder module and sealing the opening in the powder chamber of the powder module, it is possible that the gas pressure inside the powder chamber can be controlled via the build material handling unit.

The connection element preferably comprises a first opening for moving build material into or out of the powder chamber and a second opening for controlling the gas pressure in the process chamber, wherein the first and second opening can be independently opened and closed. Therefore, it is possible that the build material may be moved into the powder chamber or out of the powder chamber via the first opening, e.g. for filling fresh build material into the powder chamber. The second opening is provided for controlling the pressure in the process chamber, e.g. by guiding gas into the process chamber or removing gas from the process chamber through the second opening. It is possible to open and close the first and the second opening independent of each other. For example, it is possible that the first opening can be moved to an open state while the second opening is closed in that build material can be moved into the powder chamber without interfering with the filling process step, e.g. by sucking build material through the second opening out of the powder chamber. After the filling process step has been completed, the first opening can be closed and the second opening can be opened to control the gas pressure inside the powder chamber. It is particularly preferred that the filling of build material and the control of gas pressure is performed alternatingly for achieving the best results.

For example, the first opening may be connectable or connected to a build material handling device, in particular a sieving station. In such a build material handling device, e.g. a sieving station, (used) build material can be (pre- or post-) processed for using the build material in an additive manufacturing process. Typically, non-consolidated build material that has been removed from an additive manufacturing apparatus after an additive manufacturing process has been finished, is post-processed (or preprocessed) in that the build material is sieved for removing oversized particles, e.g. (partially) consolidated particle conglomerates. After the sieving process is finished, the build material may be provided to a powder chamber of a powder module to be used in another additive manufacturing process. Hence, the first opening of the build material handling unit may be connected to a build material handling device for receiving fresh build material that can be stored in the powder chamber of the powder module to be used in another additive manufacturing process.

The second opening of the build material handling unit, as described before, can be connected or connectable to a pump unit. The pump unit is preferably adapted to control the gas pressure inside the powder chamber, e.g. by generating an overpressure or a negative pressure in the powder chamber, as described before. To apply the corresponding pressure, the pump unit is adapted to move gas, in particular inert gas, such as argon, into the powder chamber or remove gas from the powder chamber. The pump unit may involve or be connected to a suitable reservoir or storage unit, such as a gas container, in which the gas that is to be moved (temporarily) into the powder chamber or removed therefrom, can be stored.

According to another embodiment, the build material handling unit may be built as a separate, in particular modular, build material handling station, or integrated in at least one functional unit of the plant for additively manufacturing three-dimensional objects, preferably a powder silo or a powder module, in particular a dose module, or an apparatus for additively manufacturing three-dimensional objects. In general, the build material handling unit may be integrated in one functional component of a plant for additively manufacturing three-dimensional objects, for example a handling station in which build material is sieved after an additive manufacturing process is finished. It is also possible to integrate the build material handling unit in at least one powder module of the plant or an apparatus for additively manufacturing three-dimensional objects, e.g. a mobile powder module that can be moved between at least two functional units of the plant, such as a handling station and an apparatus for additively manufacturing three-dimensional objects. Further, it is possible that any other powder module, e.g. a module with a powder chamber, such as a powder silo, can be provided with a build material handling unit for enhancing the storage capacity of the respective powder chamber.

It is also possible that the build material handling unit forms a separate modular build material handling station to which the powder module can be brought for refilling the powder module, wherein during the refilling process the build material in the powder chamber of the powder module can be leveled and compacted. Preferably, the refilling process, the compacting process and the leveling process can be performed simultaneously or alternatingly, respectively, wherein the steps of filling build material into the powder chamber, compacting and leveling the build material via the control of the gas pressure inside the powder chamber and filling additional build material into the powder chamber onto the already compacted and leveled build material can be performed alternatingly until the powder chamber is filled to a defined fill level, preferably entirely filled.

Thus, it is possible to significantly increase the volume of build material that can be received within the powder chamber, as the build material can be compacted and leveled by controlling the gas pressure inside the powder chamber. Subsequently, more build material can be filled on top of the already compacted and leveled build material, which additional amount of build material can also be compacted and leveled in that more space is generated for receiving more build material. Thus, it is possible to successively fill the powder chamber with build material which is compacted and leveled until the powder chamber is full. Basically, every container or receiving unit in which build material can be stored can be provided with or connected with a build material handling unit, as described before.

The inventive build material handling unit may further be improved by providing a determination unit that is adapted to determine the distribution parameter, in particular an evenness, and/or a compaction parameter, in particular a density, of build material in the powder chamber. Thus, it is possible to provide a determination unit via which it is possible to determine the distribution and the compaction of the build material which is arranged in the powder chamber of the powder module.

The distribution parameter may relate to the evenness of the build material in the powder chamber, e.g. how well the build material is leveled or whether irregularities in the surface of the build material are still present in the powder chamber. Further, the determination unit may be used to determine a compaction parameter that relates to the density or the degree of compaction of the build material in the powder chamber, respectively. For example, if a powder module is connected or coupled with the build material handling unit it is possible to use the determination unit to determine whether a further compaction or leveling of the build material inside the powder chamber is necessary. Further, it is possible to derive how far the leveling process and/or the compaction process of the build material arranged in the powder chamber is proceeded. For example, it is possible to control the gas pressure inside the powder chamber dependent on the distribution parameter and/or the compaction parameter.

Besides, the invention relates to a build material handling station for a plant for additively manufacturing three-dimensional objects, wherein the build material handling station comprises an inventive build material handling unit, as described before. The build material handling station may, for example, be regarded as separate unit of the plant to which the powder module can be moved for refilling the powder chamber with fresh or sieved build material. It is also possible that the build material handling station is integrated in another functional component of the plant, e.g. in an apparatus for additively manufacturing three-dimensional objects.

The build material handling station preferably comprises a moving unit which is adapted to move, in particular to lift, a powder module between an unconnected position in which the powder module is not connected with the build material handling unit and a connected position in which the powder module is connected with the build material handling unit. For example, it is possible that the powder module may be moved to the build material handling station that comprises, as described before, a build material handling unit.

The build material handling unit can be brought in contact with the powder module by lifting or moving, respectively, the powder module into the connected position. In the connected position the connection element of the build material handling unit is connected to the powder module and preferably seals the opening of the powder chamber of the powder module. After the filling process of build material and compacting and leveling the build material in the powder chamber is finished, the powder module may again be brought to the unconnected position in which the powder module is not connected with the build material handling unit. Of course, the powder module may comprise a lid that seals the opening of the powder chamber for protecting the inert environment inside the powder chamber, e.g. during transport of the powder module to the build material handling station or from the build material handling station to another station, such as an additive manufacturing apparatus.

The build material handling station is preferably adapted to alternatingly compact and/or leveled the build material in the powder chamber and fill build material into the powder chamber. Hence, the refilling process may be subdivided into at least two process steps that can be alternatingly performed, wherein in a first step of the refilling process, build material may be provided/filled into the powder chamber. Afterwards, the build material that has been filled into the powder chamber can be compacted and/or leveled, wherein subsequently, additional build material can be filled into the powder chamber. Thus, it is possible to successively increase the amount of build material that can be received in the powder chamber, as the build material that has been filled into the powder chamber is leveled and compacted, thereby generating additional space inside the powder chamber in which an additional volume of build material can be received.

Further, the invention relates to a method for handling build material for an apparatus for additively manufacturing three-dimensional objects, wherein build material handling units is coupled with a powder module and the gas pressure inside the powder chamber is controlled for leveling and/or compacting the volume of build material which is arranged inside the powder chamber of the powder module. In particular, it is possible to perform the inventive method on the inventive build material handling station and the build material handling unit, as described before.

It is particularly preferred that a volume of build material is iteratively and alternatingly filled into the powder chamber and the gas pressure in the powder chamber is controlled for leveling and/or compacting the volume of build material in the powder chamber, in particular by reducing the gas pressure and again increasing the gas pressure before the next volume of build material is filled into the powder chamber.

In other words, it is possible to connect a powder module to the build material handling unit or the build material handling station comprising a build material handling unit, respectively. After the powder module has been connected to the build material handling unit build material can be filled into the powder chamber of the build material handling unit, for example to a first fill level. The build material being filled into the powder chamber of the powder module is initially not compacted and not leveled. Thus, after the first filling step in which build material is filled into the powder chamber, the gas pressure in the powder chamber can be controlled, in particular a negative pressure can be applied.

Hence, the build material received in the powder chamber is compacted and leveled due to the negative pressure applied via the build material handling unit, e.g. to a second fill level which is below the first fill level. In the next step, the gas pressure can again be controlled to reach the initial value, e.g. ambient pressure or a slight overpressure. In the next step additional build material can be filled into the powder chamber, in particular onto the already compacted and leveled build material received in the powder chamber, e.g. to a third fill level which is above the first fill level. Subsequently, the gas pressure can again be controlled, for example by applying a negative pressure in the powder chamber, wherein due to the leveling and compaction a fourth fill level can be reached which lies above the first and second, but below the third fill level, for instance. Thus, the volume of build material steadily is increased, but due to the compaction and leveling steps, the fill level may be reduced to provide more space for additional build material. The steps of filling build material in the powder chamber and controlling the gas pressure in the powder chamber can be alternatingly and successively be performed until the build material in the powder chamber reaches a defined fill level.

Self-evidently, all details, features and advantages described with respect to the inventive build material handling unit and the inventive build material handling station and the inventive method for handling build material can be arbitrarily combined, exchanged and transferred. As described before, the inventive method may be performed on the inventive build material handling station, preferably involving an inventive build material handling unit.

Figure 2:
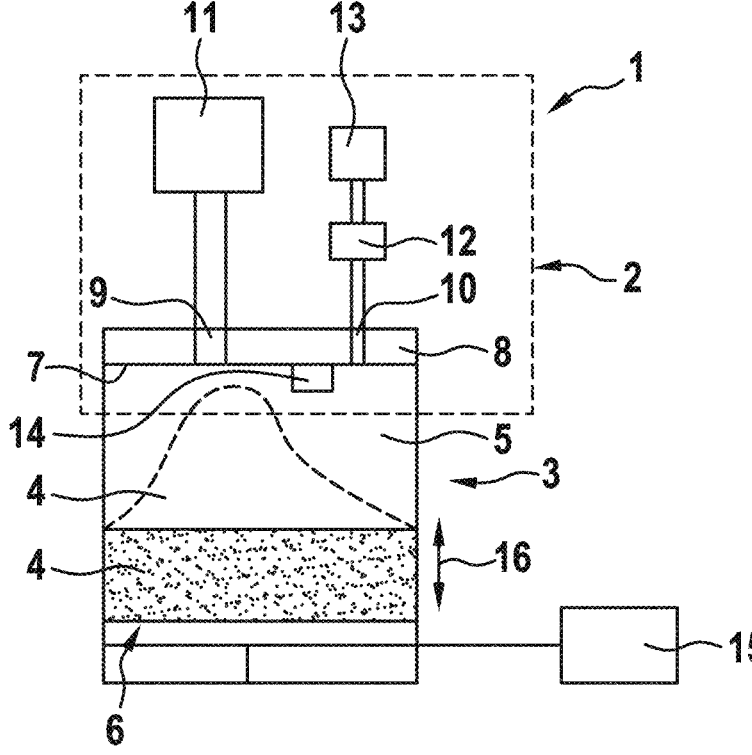

Exemplary embodiments of the invention are described with reference to the FIG. The FIG. are schematic diagrams, wherein FIG. 1 shows an inventive build material handling station with an inventive build material handling unit; and FIG. 2 shows the inventive build material handling station from FIG. 1.

FIG. 1 shows a build material handling station 1 comprising a build material handling unit 2 for a powder module 3 for an apparatus for additively manufacturing three-dimensional objects (not shown). Preferably the apparatus is adapted to successively layerwise selectively irradiate and consolidate layers of a build material 4 which can be consolidated by means of an energy source (not shown).

The powder module 3 comprises a powder chamber 5 in which the build material 4 can be received, e.g. for providing the build material 4 in an additive manufacturing process. For example, the powder module 3 comprises a carrying unit 6 for height-adjustably carrying the build material 4, wherein build material 4 may be provided in an additive manufacturing process by raising the carrying unit 6 and thereby, providing build material 4 through an opening 7 of the powder chamber 5, e.g. to a dose plane.

In the embodiment that is depicted in FIG. 1, the powder module 3 is coupled with the build material handling unit 2, in particular connected with a connection element 8 of the build material handling unit 2. In the connected state the connecting element 8 seals the opening 7 of the powder chamber 5 of the powder module 3. The connecting element 8 comprises a first opening 9 and a second opening 10, wherein the first opening 9 and the second opening 10 can be independently opened and closed, e.g. via corresponding valves (not shown). The first opening 9 is connected to a sieving unit 11 via which fresh or sieved build material 4 can be provided and filled into the powder chamber 5. In the situation that is depicted in FIG. 1, powdery build material 4 is filled into the powder chamber 5 generating a pile of build material 4 that is not compacted and not leveled.

For compacting and leveling the pile of build material 4 that has been filled into the powder chamber 5, the first opening 9 can be closed and the second opening 10 can be opened. The second opening 10 is connected to a pump unit 12 that is adapted to control the gas pressure inside the process chamber 5, in particular to apply a negative pressure in the powder chamber 5 by removing gas from the powder chamber 5. Therefore, the pump unit 12 sucks gas out of the powder chamber 5 and stores the gas in a storage unit 13, e.g. a gas container, wherein due to of the applied negative pressure, the build material 4 is leveled and compacted, as depicted in FIG. 2. After the leveling and compaction process has been finished, the pump unit 12 can be controlled correspondingly for releasing the gas from the storage unit 13 back into the powder chamber 5 for restoring the initial pressure. Subsequently, the second opening 10 may be closed and the first opening 9 may be opened to again fill additional build material 4 into the powder chamber 5, as depicted via a dashed contour in FIG. 2.

The steps of filling the build material 4 into the powder chamber 5 and compacting and leveling the build material 4 in the powder chamber 5 can be repeated alternatingly until a defined fill level of build material 4 is achieved in the powder chamber 5. The build material handling unit 2 therefore comprises a determination unit 14 which is adapted to determine the fill level, preferably via a distribution parameter, in particular an evenness, and/or a compaction parameter, in particular a density, of the build material 4 in the powder chamber 5. In other words, it is possible to derive via the determination unit 14, whether the build material 4 inside the powder chamber 5 is properly leveled and compacted. It is also possible to determine the fill level of the build material 4. Hence, the leveling and compaction process can be performed dependent on the distribution parameter and the compaction parameter determined via the determination unit 14.

The determination unit 14 may therefore, be built as or comprise a fill level indicator that is adapted to determine a top of the build material 4, e.g. the top of the cone. Additionally or alternatively, it is possible to determine the weight of the build material 4 inside the powder chamber 5, e.g. via a weighing element provided by or connected with the determination unit 14. The weighing element may therefore, determine the weight of the build material 4 resting on the carrying unit 6 or the weight of the entire powder module 3. It is also possible to use the determination unit 14 for determining the pressure inside the powder chamber 4 for determining parameters of the leveling and compacting process. In particular, the determination unit 14 may comprise a pressure sensitive element.

The build material handling station 1 further comprises a moving unit 15 which is adapted to move, in particular to lift, the powder module 3 and thereby, connect the powder module 3 with the connecting element 8 of the build material handling unit 2 or disconnect the powder module 3 from the connecting element 8 of the build material handling unit 2. The movement that can be performed via the moving unit 15 is depicted via an arrow 16 indicating that the powder module 3 may be lifted upwards to connect the powder module 3 with the build material handling unit 2 or that the powder module 3 can be moved downwards to disconnect the powder module 3 from the build material handling unit 2.

Advantageously, it is possible that the build material 4 is compacted and leveled without the need for complex mechanical setups, such as rakes or blades or other components used to mechanically interact with the build material 4 to compact and level the build material 4 inside the powder chamber 5. As powder module 3 any arbitrary container can be used in which a powder chamber 5 is provided for receiving build material 4 in which the gas pressure can be controlled. The powder module 3 may also be integrated into a component of an apparatus for additively manufacturing three-dimensional objects, such as a static powder module 3 or a mobile powder module 3 that can be releasably connected with the additive manufacturing apparatus.

It is also possible that the powder module 3 is built as other type of storage container, such as a powder silo, in which build material 4 can be (temporarily) stored. Due to the build material handling unit 2 it is possible to increase the effective capacity of the powder chamber 5, as build material 4 may be compacted and leveled and therefore, space can be generated or the available space in which build material 4 can be stored is effectively increased, respectively.

Of course, the inventive method may be performed on the inventive build material handling station 1, preferably using the inventive build material handling unit 2.

The invention claimed is:

1. A method for handling a build material for an apparatus for additively manufacturing three-dimensional objects, the method comprising:

coupling a build material handling unit comprising a connection element with a powder module, and controlling a gas pressure inside a powder chamber of the powder module for leveling and/or compacting a volume of the build material arranged inside the powder chamber of the powder module.

2. The method according to claim 1, further comprising:

repeatedly filling the volume of the build material into the powder chamber, and controlling the gas pressure in the powder chamber for leveling and/or compacting the volume of the build material in the powder chamber by reducing the gas pressure and again increasing the gas pressure before a next volume of build material is filled into the powder chamber.

3. The method according to claim 1, further comprising generating a vacuum inside the powder chamber.

4. The method according to claim 1, further comprising generating a leveling state within the powder chamber with a negative pressure between 0.7-1 bar.

5. The method according to claim 1, further comprising generating a leveling state within the powder chamber with a negative pressure between 0.8-0.9 bar.

6. The method according to claim 1, further comprising generating a compacting state within the powder chamber with a negative pressure between 0.01-1 bar.

7. The method according to claim 1, further comprising generating a compacting state within the powder chamber with a negative pressure between 0.1-0.9 bar.

8. The method according to claim 1, further comprising connecting the build material handling unit with the powder module with the connection element.

9. The method according to claim 8, wherein the connection element comprises a connection plate, and further wherein connecting the build material handling unit with the powder module with the connection element comprises connecting the build material handling unit with the powder module with the connection plate.

10. The method according to claim 1, further comprising connecting the build material handling unit with the powder module with the connection element to seal an opening of the powder chamber of the powder module.

11. The method according to claim 1, further comprising connecting the build material handling unit with the powder module with the connection element, wherein the connection element comprises a first opening for moving build material into or out of the powder chamber and a second opening for controlling the gas pressure in the powder chamber, and further comprising independently opening the first opening and the second opening.

12. The method according to claim 11, further comprising connecting the first opening to a sieving station.

13. The method according to claim 11, further comprising connecting the second opening to a pump unit.

14. The method according to claim 1, further comprising determining a distribution of the build material in the powder chamber.

15. The method according to claim 14, wherein determining the distribution comprises determining an evenness, a compaction parameter, and/or a density of the build material in the powder chamber.

* * * * *